(12) United States Patent
Wagner

(10) Patent No.: US 7,760,357 B2
(45) Date of Patent: Jul. 20, 2010

(54) TACHYONIZED MATERIAL TEST METHOD

(76) Inventor: David Wagner, 480 Tosconi Cir., Santa Rosa, CA (US) 95401

( * ) Notice: Subject to any disclaimer, the term of this patent is extended or adjusted under 35 U.S.C. 154(b) by 269 days.

(21) Appl. No.: 12/141,463

(22) Filed: Jun. 18, 2008

(65) Prior Publication Data
US 2009/0316154 A1    Dec. 24, 2009

(51) Int. Cl.
*G01J 4/00* (2006.01)
*C12Q 1/02* (2006.01)
*C12N 9/50* (2006.01)

(52) U.S. Cl. .................... 356/366; 356/364; 435/29; 435/219

(58) Field of Classification Search ......... 356/364–370; 435/4, 7.22, 7.92, 29, 34, 219; 424/94.6
See application file for complete search history.

(56) References Cited

U.S. PATENT DOCUMENTS 5,698,411 A * 12/1997 Lucas et al. .................... 435/29
5,849,513 A * 12/1998 Jaffe et al. ..................... 435/29
2004/0170618 A1* 9/2004 Davis et al. ................. 424/94.6

* cited by examiner

*Primary Examiner*—Sang Nguyen
(74) *Attorney, Agent, or Firm*—Edward S. Sherman

(57) ABSTRACT

Many suppliers claimed their products have been Tachyonized™ since the discovery and commercialization of Tachyonized™ products by Advanced Tachyon Technologies International. Genuine materials that have been Tachyonized have demonstrated a range of beneficial properties to biological organisms and processes. However, the market has been saturated with competitors making such claims without any foundation. Accordingly, the inventive process provides a simple and rapid test method to confirm the authenticity of Tachyonized materials.

4 Claims, 1 Drawing Sheet

US 7,760,357 B2

TACHYONIZED MATERIAL TEST METHOD

CROSS REFERENCE TO RELATED APPLICATIONS

None

BACKGROUND OF INVENTION

The present invention relates to a method of testing materials that have been tachyonized or otherwise at least claim to harness tachyon energy for beneficial purposes.

The benefits of Tachyonized™ materials for holistic healing are disclosed in, among other sources, in "Tachyon Energy", by David Wagner and Gabriel Cousines, M. D., North Atlantic Books, Berkeley, Calif. 1999, which is incorporated herein by reference.

Further, the theoretical basis for the tachyon particle is described "The Physics of Tachyons", by Ernst L. Wall, Hadronic Press, Palm Harbour, Fla., 1995, which is incorporated herein by reference.

Materials are referred to as "Tachyonized" when they have undergone a proprietary treatment. The treatment is believed to enable the harnessing of tachyon energy by the materials, so then when the material is placed near living objects biological effects are observed, in particular healing effects in living organisms over an extended period of time. For example, the original supplier and developer of Tachyonized materials, Advanced Tachyon Technologies, states in its literature and website:

"The use of Tachyonized products normally results in a natural detoxification, increased absorption of available vitamins and minerals, increased energy for physical activities, increased awareness of subtle energies, increased brain function, increased circulation, and exceptional improvements in athletic abilities and muscle recovery. When athletes use these products, they notice a significant decrease in fatigue, allowing for increased performance."

Many commercial suppliers offer what are claimed to be Tachynized materials for sale. While non-biological effects of genuine Tachyonized material can be observed by such means as Kirlian photography, this takes time and requires expensive equipment.

Accordingly, there is a need for a rapid and simple test for medical practitioners and consumers that distinguishes genuine from counterfeit Tachyonized material. Further, to the extent new inventions, discoveries and improvement are made in methods of Tachyonizing materials, there is a need to provide a test method to confirm the efficacy, quality and yield of such methods.

Thus, it is an object of the present invention to provide such a test method.

SUMMARY OF INVENTION

In the present invention, the object is achieved by a method comprising the steps of providing an alleged Tachyonized material, providing a salt solution, placing a quantity of the salt solution on a substrate for microscopy, evaporating the solvent from the salt solution while the substrate is placed on or adjacent to the Tachyonized material, and then observing the crystal morphology of the salt on the substrate for microscopy with a microscope, the observation being made relative to salt crystallized in the same manner but in the absence of the alleged Tachyonized material.

The above and other objects, effects, features, and advantages of the present invention will become more apparent from the following description of the embodiments thereof taken in conjunction with the accompanying drawings.

DETAILED DESCRIPTION

In accordance with the present invention, the following tests were performed to demonstrate that genuine Tachyonized materials can be distinguished from substitutes.

First, 20 drops of reverse osmosis purified water was placed in a sterile Petri dish. Then about 10 small sodium chloride crystals (ACS reagent grade) were mixed with the water until completed dissolved. 10 clean sterile slides were set aside for evaporation tests, with 5 marked as control and 5 as the test material (T). From the same source Petri dish, one drop of the above salt solution was removed and then placed on each of the 10 clean sterile slides.

The "T" labeled slides were immediate placed on a Tachyonized TLC Bar that was 4 inches in diameter that was obtained from Advanced Tachyon Technologies of Santa Rosa, Calif. (SKU TLC-M). Similar results were obtained with the SD-U4 ultra disk form the same source.

The 5 control slides were kept at least 70 feet away from the Tachyonized material. Once the water had completely evaporated, the slides were viewed in an orb polarized light microscope in transmission mode and representative photographs were then recorded, and are described below with respect to FIG. 1 and FIG. 2.

Figure 1:
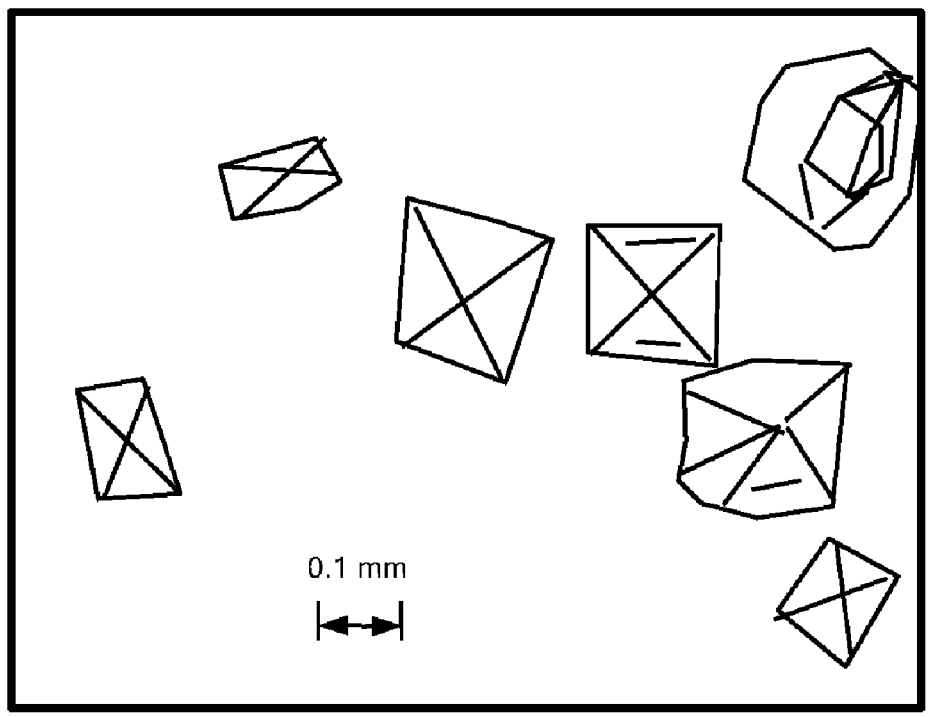
FIG. 1 is a black and white line drawing depicting the salient features observed in polarizing microscope image of a control sample of salt evaporated without the inventive treatment.

FIG. 1 is a black and white line drawing to schematically illustrate the salient and representative features observed in an actual micrograph of a control sample. These control conditions results in large salt crystals generally having a double pyramid crystal habit shaped well dispersed on the slide, having a size range of from about 100 microns to about 200 microns.

Figure 2:
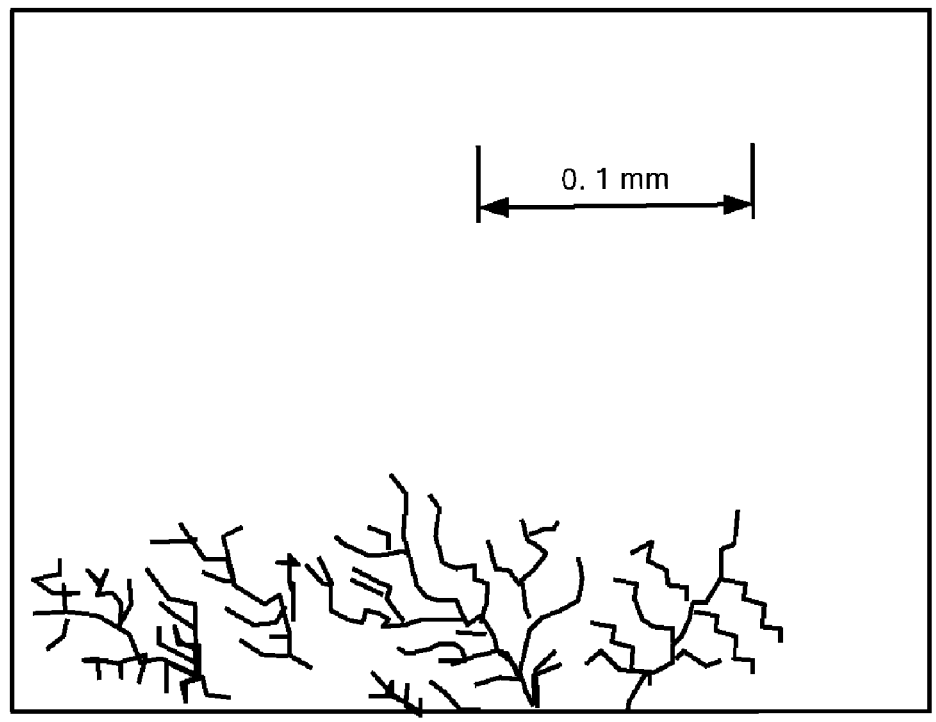
FIG. 2 is a black and white line drawing depicting the salient features in a polarizing microscope image of salt evaporated with the inventive treatment.

FIG. 2 is a black and white line drawing to schematically illustrate the salient and representative features observed in an actual micrograph of salt crystallized while exposed to the Tachyonized materials described above. The micrograph was taken at higher magnification, as the large salt crystals observed in FIG. 1 were not present and do not form when crystallization occurs in the after this treatment. Only a portion of the actual micrograph is depicted, as it was difficult to obtain a greater portion of the field in sharp enough focus to accurately depict the characteristic features. These features are a dendrite crystal microstructure of much smaller polycrystalline aggregates. The dendrite branches have a diameter of about 5 microns or less.

Further, it should be noted that this microstructure can also be observed in the control samples of FIG. 1 when viewed at higher magnification between the larger salt crystals. Thus, the distinctive feature of the crystallization of salts in the presence of a Tachyonized material is the absence of larger salt crystals having a regular crystal habit.

In observing the crystallization process in the presence of Tachyonized materials is was also observed that as water evaporates the larger crystal appear to nucleate but then dissolve or disappear before evaporation is complete leaving behind only dendritic structures such as that shown in FIG. 2. The absence of the large salt crystals in such comparative evaporative tests of salts identifies the genuine Tachyonized material as the substrate whose presence during crystallization precludes the formation of the large salt crystals that form in the Tachyonized materials absence.

Not wishing to be bound by theory, it is believed that Tachyonized materials may disrupt ionic bonds between oppositely charged ions before they can become bound into crystals during the crystallization process.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

For examples, based on the above findings it is believed that the test method for can be carried out with other inorganic salts than sodium chloride, as well as mixed inorganic and organic salts. It will be apparent to one of ordinary skill in the art that range of test material can be readily expanded without undue experimentation, as the test method disclosed herein is very simple and rapid Likewise, while the use of polarized light microscopy facilitated the observation of the sodium chloride salt crystals of different morphologies, other forms of optical microscopy and electronic microscopy may be deployed, as will be evident to one of ordinary skill in the art depending on the type of crystalline substance deployed as the test material.

The invention claimed is:

1. A method of detecting and confirming the authenticity of Tachyonized material, the method comprising the steps of:
   a) providing the alleged Tachyonized material,
   b) providing a salt solution,
   c) placing a quantity of the salt solution on a substrate for microscopy,
   d) evaporating the solvent from the salt solution while the substrate is placed on or adjacent to the alleged Tachyonized material,
   e) observing an crystal morphology of the salt on the substrate for microscopy with a microscope, and
   f) comparing the crystal morphology of the salt on a substrate with that of salt crystallized in the absence of the alleged Tachyonized material.

2. The method of detecting and confirming the authenticity of Tachyonized material according to claim 1 wherein the salt solution comprises sodium chloride and the solvent is water.

3. The method of detecting and confirming the authenticity of Tachyonized material according to claim 1 wherein said step of observing the crystal morphology comprises illuminating the samples with polarized light and viewing the light transmitted through a polarizing analyzer.

4. The method of detecting and confirming the authenticity of Tachyonized material according to claim 2 wherein said step of observing the crystal morphology comprises illuminating the samples with polarized light and viewing the light transmitted through a polarizing analyzer.

* * * * *